United States Patent [19]

Cooper et al.

[11] Patent Number: 4,551,466

[45] Date of Patent: Nov. 5, 1985

[54] PYRIDYL-2-OXY-PROPYL-1H-1,2,4-TRIAZOLE-3,5-DIAMINES

[75] Inventors: David G. Cooper, Letchworth; George S. Sach, Welwyn, both of England

[73] Assignee: Smith Kline & French Laboratories Limited, Welwyn Garden City, England

[21] Appl. No.: 473,519

[22] Filed: Mar. 9, 1983

[30] Foreign Application Priority Data

Mar. 17, 1982 [GB] United Kingdom ................ 8207835
Mar. 31, 1982 [GB] United Kingdom ................ 8209540

[51] Int. Cl.$^4$ .................. C07D 401/12; C07D 401/14; A61K 31/445
[52] U.S. Cl. .................................... 514/318; 514/343; 514/340; 546/276; 546/193
[58] Field of Search ................ 546/276, 193; 424/263

[56] References Cited

U.S. PATENT DOCUMENTS 4,252,819 2/1981 Hirata et al. .................... 546/278
4,318,913 3/1982 Clitherow et al. ................ 546/194
4,411,899 10/1983 Baldwin et al. .................... 546/209

OTHER PUBLICATIONS

Derwent Abstract 29067E (EP 49173).
Derwent Abstract 20656D (Netherlands 8004967).
Derwent Abstract 269K (EP 67436).

Primary Examiner—Jane T. Fan
Attorney, Agent, or Firm—Joan S. Keps; Richard D. Foggio; Alan D. Lourie

[57] ABSTRACT

This invention relates to diaminotriazole derivatives in which one amino group is substituted by a 4-dialkylamino- or piperidinyl- or pyrolidinylmethyl pyrid-2-yloxypropyl group. The compounds have histamine H$_2$-antagonist activity. One specific compound is 1-methyl-N$^5$-3-(4-[1-piperidinomethyl]-pyridyl-2-oxy)-propyl-1H-1,2,4-triazole-3,5-diamine.

12 Claims, No Drawings

PYRIDYL-2-OXY-PROPYL-1H-1,2,4-TRIAZOLE-3,5-DIAMINES

This invention relates to certain pyridine derivatives, processes for their preparation, pharmaceutical compositions containing them and their use as histamine $H_2$-antagonists.

A histamine, a physiologically active compound endogenous in mammals, exerts its action by interacting with certain sites called receptors. One type of receptor is known as a histamine $H_1$-receptor (Ash and Schild, Brit. J. Pharmac. Chemother. 27 427(1966)) and the actions of histamine mediated through these receptors are blocked by drugs commonly called "antihistamines" (histamine $H_1$-antagonists) a common example of which is mepyramine. A second type of histamine receptor is known as the $H_2$-receptor (Black et al. Nature 1972, 236, 385). These receptors are not blocked by mepyramine but are blocked by burimamide. Compounds which block these histamine $H_2$-receptors are called histamine $H_2$-antagonists.

Histamine $H_2$-antagonists are useful in treating disease conditions caused by the biological effects of histamine mediated through $H_2$-receptors, for example, as inhibitors of gastric acid secretion, in the treatment of inflammation mediated through histamine $H_2$-receptors and as agents which act on the cardiovascular system, for example, as inhibitors of effects of histamine on blood pressure mediated through histamine $H_2$-receptors.

Cimetidine is an example of a histamine $H_2$-antagonist. Cimetidine has been shown to be useful in the treatment of duodenal, gastric, recurrent and stomal ulceration, and reflux oesophagitis and in the management of patients who are at high risk from haemorrhage of the upper gastrointestinal tract.

In some physiological conditions the biological actions of histamine are mediated through both histamine $H_1$- and $H_2$-receptors and blockade of both types of receptors is useful. These conditions include inflammation mediated by histamine, for example skin inflammation, and those hypersensitivity responses due to the action of histamine at $H_1$- and $H_2$-receptors, for example allergies.

According to the present invention there is provided compounds of formula (1):

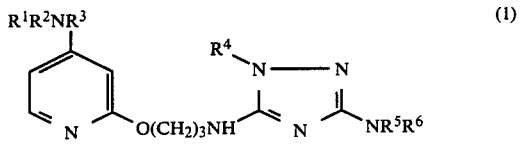

and pharmaceutically acceptable salts thereof, where
$R^1$ and $R^2$ are the same or different and are $C_{1-6}$ alkyl or with the nitrogen atom to which they are attached form a pyrrolidino or piperidino group;
$R^3$ is $C_{1-4}$ alkylene;
$R^4$ is hydrogen, $C_{1-6}$ alkyl, hydroxy-$C_{2-4}$ alkyl; optionally substituted phenyl or phenyl ($C_{1-6}$ alkyl) (the substituents being one or more $C_{1-6}$ alkyl, or $C_{1-6}$ alkoxy groups or halogen atoms);
$R^5$ and $R^6$ are the same or different and are hydrogen, $C_{1-6}$ alkyl, hydroxy $C_{2-6}$ alkyl, $C_{1-6}$ alkoxy-$C_{1-6}$ alkyl, $C_{2-6}$ alkenyl, $C_{2-6}$ alkynyl, optionally substituted phenyl or phenyl ($C_{1-6}$ alkyl), (the substituents being one or more $C_{1-6}$ alkyl or $C_{1-6}$ alkoxy groups or halogen atoms or a methylenedioxo group), or optionally substituted furanyl- or thienyl- or pyridyl($C_{1-6}$ alkyl) (the substituents being one or more $C_{1-6}$ alkyl or $C_{1-6}$ alkoxy groups); or taken together represent a $C_{4-6}$ alkylene group, or taken together represent a group of formula (2):

$$=CR^7R^8 \qquad (2)$$

where
$R^7$ is phenyl or pyridyl and $R^8$ is hydrogen or $C_{1-6}$ alkyl.

The presence of the group $R^1R^2NR^3$ at position 4 of the 2-pyridyl moiety in the compounds of formula (1) confers a particularly favourable level of $H_2$-antagonist activity.

Examples of $C_{1-6}$ alkyl groups which $R^1$ and $R^2$ represent are methyl, ethyl, n-propyl and iso-propyl. $R^1$ and $R^2$ can be the same $C_{1-6}$ alkyl group and in particular they are methyl.

Examples of alkylene groups which $R^3$ represents are methylene, ethane-1,2-diyl and propane-1,3-diyl. Preferably $R^3$ is methylene. In particular the group $R^1R^2NR^3$ is dimethylaminomethyl, preferably it is 1-piperidinomethyl.

Examples of $C_{1-6}$ alkyl groups for $R^4$ are methyl, ethyl and n-propyl (particularly methyl).

Examples of $C_{1-6}$ alkoxy-$C_{1-6}$ alkyl groups for $R^4$ are methoxyethyl, ethoxymethyl, ethoxypropyl, and propoxymethyl.

Examples of $C_{3-6}$ alkenyl groups for $R^4$ are 2-propenyl and 2-butenyl.

Examples of hydroxy-$C_{2-4}$ alkyl groups for $R^4$ are 2-hydroxyethyl and 3-hydroxypropyl (particularly 2-hydroxyethyl).

Examples of substituted phenyl groups and the substituted phenyl moiety of the phenyl($C_{1-6}$ alkyl) groups for $R^4$ are 3-methylphenyl, 3-methoxyphenyl, 3,4-dimethoxyphenyl and 3-chlorophenyl.

Examples of $C_{1-6}$ alkyl groups for $R^5$ and $R^6$ are methyl, ethyl and n-propyl.

Examples of $C_{2-6}$ alkynyl groups for $R^5$ and $R^6$ are ethynyl, 2-propynyl and 3-butynyl.

Examples of hydroxy-$C_{1-6}$ alkyl groups for $R^5$ and $R^6$ are 3-hydroxypropyl, 4-hydroxybutyl and in particular 5-hydroxypentyl.

Examples of $C_{1-6}$alkoxy-$C_{1-6}$alkyl groups for $R^5$ and $R^6$ are ethoxyethyl, ethoxymethyl and in particular methoxyethyl.

Examples of substituted phenyl groups and the substituted phenyl moiety of the phenyl($C_{1-6}$) alkyl groups for $R^5$ and $R^6$ are 3-methylphenyl, 3-methoxyphenyl, 3,4-dimethoxyphenyl and 3-chlorophenyl.

Examples of optionally substituted furanyl-, thienyl- and pyridyl($C_{1-6}$ alkyl) groups for $R^5$ and $R^6$ are optionally substituted 2-furanyl-, 2-thienyl-, 2-pyridyl-, 3-pyridyl-, or 4-pyridyl-($C_{1-6}$ alkyl) groups, and particularly 3-pyridyl-, 6-methyl-3-pyridyl- and 6-methoxy-3-pyridyl-($C_{1-6}$ alkyl).

When $R^5$ and $R^6$ are the same, preferably they are hydrogen, methyl, ethyl or n-propyl. Otherwise $R^5$ is preferably hydrogen and $R^6$ is as previously defined.

Examples of $C_{4-6}$ alkylene groups for $R^5$ and $R^6$ when taken together are butane-1,4-diyl and pentane-1,5-diyl. Thus by way of example $R^5$ and $R^6$ taken with the nitrogen atom to which they are attached can represent a piperidinyl or especially a pyrrolidinyl group.

Examples of substituted phenyl groups for $R^5$, $R^6$ and $R^7$ are 3-methylphenyl, 3-methoxyphenyl, 3,4-dimethoxyphenyl and 3chlorophenyl.

Examples of optionally substituted furanyl, thienyl and pyridyl groups for $R^5$ and $R^6$ are optionally substituted 2-furanyl, 2-thienyl, 2-pyridyl, 3-pyridyl, or 4-pyridyl groups, and particularly 3-pyridyl, 6-methyl-3-pyridyl and 6-methoxy-3-pyridyl.

Examples of $C_{1-6}$ alkyl groups for $R^8$ are methyl, ethyl and n-propyl.

In particular $R^7$ is phenyl, 3pyridyl or 4-pyridyl and $R^8$ is hydrogen.

Examples of particular compounds within the scope of this invention are:

1-methyl-$N^5$-3-(4-dimethylaminomethyl-pyridyl-2-oxy)propyl-1H-1,2,4-triazole-3,5-diamine;

$N^5$-3-(4-[1-piperidinomethyl]-pyridyl-2-oxy)propyl-1H-1,2,4-triazole-3,5-diamine;

1-methyl-$N^5$-3-(4-[1-piperidinomethyl]-pyridyl-2-oxy)propyl-1H-1,2,4-triazole-3,5-diamine and their pharmaceutically acceptable salts.

Examples of pharmaceutically acceptable acid addition salts of compounds of formula (1) are those formed with hydrochloric, hydrobromic, sulphuric, phosphoric, acetic, citric, maleic, lactic, ascorbic and methanesulphonic acids.

Compounds of formula (1) where $R^5$ and $R^6$ are hydrogen can be prepared by cyclising a compound of formula (3):

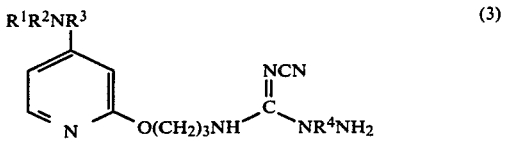

(3)

where $R^1$ to $R^4$ are as defined in formula (1).

Compounds of formula (3) can be prepared by reacting a compound of formula (4):

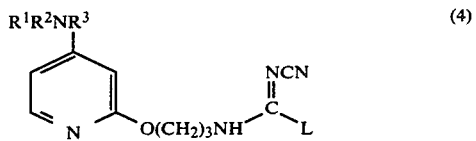

(4)

where $R^1$ to $R^3$ are as defined with reference to formula (1) and L is a leaving group displaceable with amine (for example $C_{1-6}$ alkylthio, $C_{1-6}$ alkoxy or phenoxy) with a hydrazine of formula (5):

R⁴NHNH₂ (5)

where $R^4$ is as defined with reference to formula (1).

This reaction can be carried out in the presence of a solvent for example an aromatic hydrocarbon, in particular toluene; a $C_{1-6}$ alkanol in particular ethanol or iso-propanol; water; diethyl ether or dimethylformamide. The reaction can be carried out at from room temperature to the reflux temperature of the solvent. The compound (3) forms and cyclises in situ to form the corresponding compound of formula (1).

The compounds of formula (3) can also be prepared by reacting a compound of formula (6):

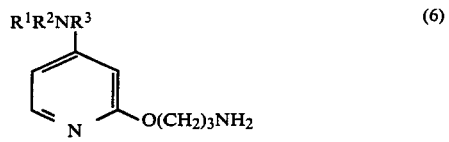

(6)

with a compound of formula (7):

(7)

or a derivative thereof where the $NH_2$ group is protected, L is a leaving group as defined with reference to formula (4) and $R^4$ is as defined with reference to formula (1) and thereafter removing any protecting group.

The reaction can be carried out optionally in the presence of a solvent for example an aromatic hydrocarbon, particularly toluene; a $C_{1-6}$ alkanol particularly methanol, ethanol or iso-propanol; acetonitrile or water. The reaction can be carried out at moderate temperatures for example from room temperature to the reflux temperature of any solvent present. The compound (3) forms and cyclises in situ to form the corresponding compound of formula (1).

One protecting group which can be used in this process is the benzylidene group. This can be removed with aqueous hydrochloric acid or by heating with an amine.

Compounds of formula (7) can be prepared by reacting a compound of formula (8):

(8)

where L is as previously defined with the hydrazine of formula (5). This reaction is preferably carried out in a solvent for example an aromatic hydrocarbon (in particular toluene), a $C_{1-6}$ alkanol (in particular methanol or ethanol), diethyl ether or acetonitrile.

The reaction of compounds of formula (8) with compounds of formula (6) and the subsequent reaction with a hydrazine of formula (5) can be carried out by analogy with the reaction described in European Patent Application No. 82300406.4.

Compounds of formula (1) where $R^5$ and $R^6$ do not represent a group of formula (2) can be prepared by cyclizing a compound of formula (9):

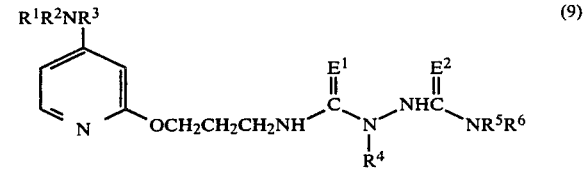

(9)

where $R^1$ to $R^6$ are as defined with reference to formula (1) except $R^5$ and $R^6$ are not a group of formula (2); $E^1$ is NH and $E^2$ is sulphur, oxygen or NH or $E^1$ is sulphur or oxygen and $E^2$ is NH.

The reaction is preferably carried out by heating the compound of formula (9) in a polar organic solvent for example acetonitrile or dimethylformamide.

Compounds of formula (9) where $E^1$ is NH and $E^2$ is sulphur, oxygen or NH can be prepared by reacting a compound of formula (10):

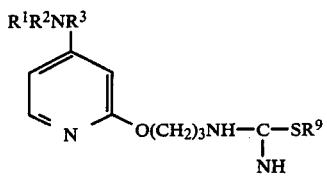
(10)

where $R^9$ is $C_{1-6}$ alkyl, with a compound of formula (11):

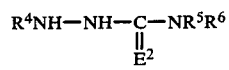
(11)

This reaction can be carried out in the presence of a solvent for example dimethylformamide.

Compounds of formula (10) can be prepared by reacting a compound of formula (12):

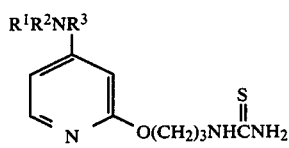
(12)

where $R^1$ to $R^3$ are as defined with reference to formula (1) with a $C_{1-6}$ alkylhalide or di-$C_{1-6}$ alkylsulphate in the presence of an acid.

Compounds of formula (9) where $E^1$ is sulphur or oxygen, and $R^5$ and $R^6$ are hydrogen or $C_{1-6}$ alkyl can be prepared by reacting a compound of formula (13):

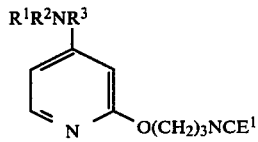
(13)

where $R^1$ to $R^3$ are as defined with reference to formula (1) and $E^1$ is sulphur or oxygen with a compound of formula (11). The reaction can be carried out in the presence of a polar organic solvent for example a $C_{1-6}$ alkanol (particularly ethanol) or acetonitrile at from room temperature to the reflux temperature of the solvent.

Compounds of formula (1) where $R^5$ and $R^6$ are other than hydrogen or a group of formula (2) can be prepared by reacting a compound of formula (14):

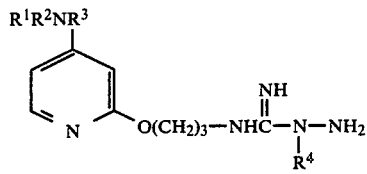
(14)

with a carbamoyl halide of formula (15):

(15)

where $R^5$ and $R^6$ are as defined with reference to formula (1).

Compounds of formula (14) can in turn be prepared by the reaction of a corresponding compound of formula (10) with a hydrazine of formula (5).

Compounds of formula (1) can be prepared by reacting a compound of formula (16):

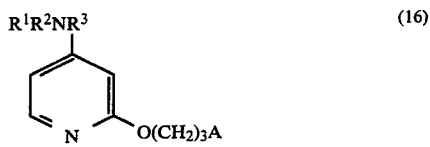
(16)

where $R^1$ to $R^3$ are as defined with reference to formula (1) and A is a group displaceable with amine, with a compound of formula (17):

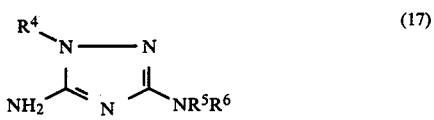
(17)

where $R^4$ to $R^6$ are as defined with reference to formula (1).

Examples of groups displaceable with amine for A are tosyloxy and mesyloxy.

Compounds of formula (1) where $R^5$ and $R^6$ represent a group of formula (2):

$$=CR^7R^8 \quad (2)$$

can be prepared by reacting the corresponding compound of formula (1) where $R^5$ and $R^6$ are both hydrogen with an aldehyde $R^7$- or $R^8$HCO or the ketone $R^7R^8$CO where $R^7$ and $R^8$ are as defined with reference to formula (1).

The reaction between the aldehyde $R^7$- or $R^8$HCO or the ketone $R^7R^8$CO can be carried out in an organic solvent, particularly an aromatic hydrocarbon (especially benzene) or a $C_{1-6}$ alkanol (especially methanol or ethanol). The reaction is preferably carried out at a moderate temperature in particular at the reflux temperature of the solvent.

Compounds of formula (1) where $R^5$ and $R^6$ are both methyl can be prepared from the corresponding compounds where $R^5$ and $R^6$ are both hydrogen by reaction with formic acid and formaldehyde.

The reaction with formic acid and formaldehyde is an example of the Eschweiler-Clarke reaction and can be carried out under conditions which are standard for such reactions.

Compounds of formula (1) can also be prepared by reacting a compound of formula (18):

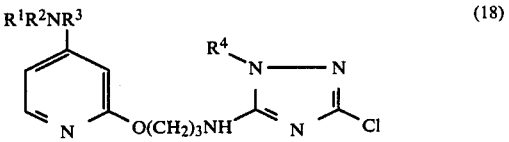
(18)

where $R^1$ to $R^4$ are as defined with reference to formula (1) with an amine of formula 19:

$$R^5R^6NH \quad (19)$$

where $R^5$ and $R^6$ are as defined with reference to formula (1).

This reaction can be carried out in a polar organic solvent for example acetonitrile and in the presence of base for example potassium carbonate.

Compounds of formula (18) can be prepared by reacting a compound of formula (1) where $NR^5R^6$ is amino with sodium nitrite with a mineral acid, particularly hydrochloric acid and reacting the diazonium salt with cuprous chloride.

Compounds of formula (6) where $R^3$ is $CH_2$ can be prepared as described in European Patent Application No. 0049173 and compounds of formula (6) where $R^3$ other than $CH_2$ can be prepared by analogous procedures. The compounds of formula (6) can be made by reducing a compound of formula (20), (21), or (22):

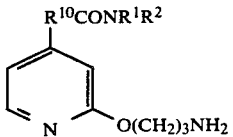
(20)

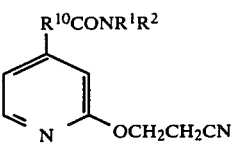
(21)

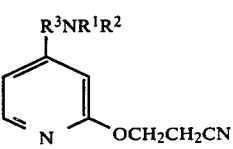
(22)

where $R^1$ to $R^3$ are as defined with reference to formula (1) and $R^{10}$ is a covalent bond or $C_{1-3}$ alkylene, using lithium aluminium hydride, or by reacting a compound of formula (23) with 3-aminopropanol under basic conditions.

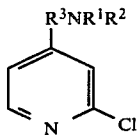
(23)

The compounds of formula (20), (21), and (22) can be prepared by reacting a compound of formula (24) or (25)

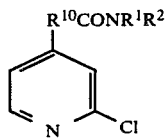
(24)

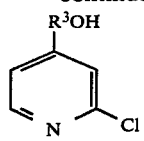
(25)

with 3-aminopropanol or 3-hydroxypropionitrile under basic conditions. The compounds of formula (23) can be prepared by successively reacting a compound of formula (25) with thionyl chloride and an amine $R^1R^2NH$.

Compounds of formula (16) where A is in particular tosyloxy and mesyloxy can be prepared by reacting a compound of formula (26):

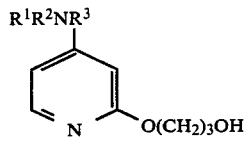
(26)

where $R^1$ to $R^3$ are as defined with reference to formula (1) with p-toluenesulphonic acid or methanesulphonic acid or an acid chloride or activated ester derivative thereof.

Compounds of formula (26) can in turn be prepared by reacting compounds of formula (23) or (24) with 1,3-propanediol in the presence of base.

Compounds of formula (12) above can be prepared by reacting the corresponding compound of formula (6) with benzoylthioisocyanate and thereafter hydrolysing the product with aqueous potassium carbonate.

Compounds of formula (3), (4), (9), (10), (13), (14) and (18) can be prepared by analogy with procedures described in British Patent Application No. 2023133A.

Compounds of formula (17) are known and can be prepared by known methods as described in British Patent Application No. 2023133A.

Acid addition salts of compounds of formula (1) can be formed from the corresponding bases by standard procedures for example by reacting the base with an acid in a $C_{1-6}$ alkanol or by the use of an ion-exchange resin. Salts of compounds of formula (1) can be interconverted using an ion-exchange resin.

The activity of the compounds of formula (1) as histamine $H_2$-antagonists can be demonstrated by their ability to inhibit histamine-stimulated secretion of gastric acid from the lumen-perfused stomachs of rats anaesthetised with urethane, and to reverse histamine-induced inhibition of contractions of the isolated rat uterus. These are actions of histamine which, according to Ash and Schild, Brit. J. Pharmac. Chemother. 27 247 (1966), are not mediated by histamine $H_1$-receptors.

The histamine $H_2$-antagonist activity of the compounds can also be demonstrated by the inhibition of histamine-stimulated acid secretion in the Heidenhain Pouch Dog, the inhibition of histamine-induced tachycardia in the isolated guinea pig right atrium and the inhibition of histamine-induced vasodilatation in the anaesthetised cat.

Inhibition of histamine-stimulated secretion of gastric acid can be measured by using a lumen-perfused stomachs of rats anesthetised with urethane using the following modification of the method of Ghosh and Schild, Brit. J. Pharmac. Chemother. 13 54 (1958):

Female Sprague-Dawley rats (160–200 g) are starved overnight and anaesthetised with urethane given intraperitoneally in one dose (200 mg). The trachea and jugular veins are both cannulated and a mid-line incision is made in the abdomen exposing the stomach which is cleared from connective tissue. A small incision is made in the rumen of the stomach and the stomach is washed with 5% w/v glucose solution. The oesophagus is partially cleared of connective tissue and cannulated with polythene tubing and the oesophagus and vagi are then cut above the cannula. An incision is made in the antrum and a cannula is passed into the stomach via the ruminal incision and through into the antrum so that the head of the cannula lies in the body of the stomach. A funnel-shaped cannula is inserted in the ruminal incision and tied into position so that the line between the rumen and the body coincides with the edge of the funnel. The antral cannula is tied into place to reduce the possibility that antrally released gastrin will effect gastric acid secretion. Two stab wounds are made in the abdominal wall, and the stomach cannulae passed through. The stomach is perfused through the oesophageal and stomach cannulae with 5.4% w/v glucose solution at 37° at 1–2 ml min$^{-1}$. The effluent is passed over a micro-flow pH electrode and recorded by a pH meter fed to an anti-log unit and flat-bed recorder. The basal output of acid secretion from the stomach is monitored by measurement of the pH of the perfusion effluent. A sub-maximal dose of histamine is continuously infused into the jugular vein and produces a stable plateau of acid secretion and the pH of the perfusion effluent is determined when this condition is obtained. Infusion of histamine at a rate of 0.25 micromol kg$^{-1}$min$^{-1}$ produces 70% of maximum histamine stimulated gastic acid secretion. The test compound is then administered intravenously into the second jugular vein and washed in with glucose solution (0.2 ml, 5.4% w/v). The difference in acid secretion between basel output and the histamine stimulated plateau level and the reduction of acid secretion caused by the test compound are calculated from the difference in pH of the perfusion effluent. ED$_{50}$ values (for inhibiting sub-maximal acid secretion by 50%) are determined by administering one dose of test compound to one rat and repeating this in at least four rats for each of three or more dose levels. The results obtained are then used to calculate the ED$_{50}$ value by the standard method of least squares.

Heidenhain pouch dogs can be prepared and used as described in European Specification 15138.

In the guinea pig atrium test a spontaneously beating isolated portion of the guinea pig right atrium is secured under tension (300 mg) between an anchorage and a transducer in a 15 ml tissue bath and immersed in Mc-Ewens solution with constant aeration at a temperature of 37° C. The output from the transducer is amplified. Output is in turn fed to a flat bed recorder. Measured amounts of histamine are added to the tissue bath so that the histamine concentration increases step-wise until the rate of beating reaches a maximum. The tissue bath is washed out and filled with fresh McEwens solution containing compound under test. The solution is left in contact with the tissue for 60 min. and measured amounts of histamine are added again until a maximum rate is recorded. The assay is repeated with increasing concentrations of test compound and the dose of histamine giving 50% of maximum rate is noted. A dose ratio (DR) was calculated by comparing the concentrations of histamine required to produce 50% maximum response in the absence and in the presence of the antagonist. A plot of Log DR-1 against LOG D (the concentration of compound under test) is made and the point of intersection with the Log (DR-1) ordinate is taken as the measure of the activity (pA$_2$ value).

To illustrate the level of activity of the compounds of the invention we have determined that the products of the Examples have ED$_{50}$ values in the lumen-perfused rat test of less than 2.0 micromol kg$^{-1}$ i.v. and pA$_2$ values in the guinea pig atrium test of more than 6.0. The ED$_{50}$ value for the compound of Example 3 is 0.14 micromol kg$^{-1}$ and the pA$_2$ value is 7.38.

In order to use compounds of formula (1) or a pharmaceutically acceptable salt thereof for medical purposes, they are normally formulated in accordance with standard pharmaceutical practice as pharmaceutical compositions.

The invention further provides pharmaceutical compositions comprising a compound of formula (1) above or a pharmaceutically acceptable acid addition salt thereof together with a pharmaceutically acceptable carrier.

Compounds of formula (1) and their pharmaceutically acceptable acid addition salts may be administered orally, parenterally, cutaneously or rectally.

Compounds of formula (1) and their pharmaceutically acceptable salts which are active when given orally can be formulated as syrups, tablets, capsules and lozenges. A syrup formulation will generally consist of a suspension or solution of the compound or salt in a suitable liquid carrier for example, ethanol, glycerine or water with a flavouring or colouring agent. Where the composition is in the form of a tablet, any suitable pharmaceutical carrier routinely used for preparing solid formulations may be used. Examples of such carriers include magnesium stearate, starch, lactose, sucrose and cellulose.

Typical parenteral compositions consist of a solution or suspension of the compound or salt in a sterile aqueous carrier or parenterally acceptable oil.

Typical compositions for administration to the skin include lotions and creams in which the compound of formula (1) or salt thereof is contained in a liquid vehicle.

A typical suppository formulation comprises a compound of formula (1) or a pharmaceutically acceptable salt thereof which is active when administered in this way, with a binding and/or lubricating agent such as gelatin or cocoa butter or other low melting vegetable waxes or fats.

Preferably the composition is in unit dose form such as a tablet or capsule.

Each dosage unit for oral administration contains preferably from 15 to 250 mg (and for parenteral administration contains preferably from 1.5 to 25 mg) of a compound of formula (1) or a pharmaceutically acceptable salt thereof calculated as the free base.

The invention also provides a method of blocking histamine H$_2$ receptors which comprises administering to an animal an effective amount to block said receptors of a compound of formula (1) or a pharmaceutically acceptable acid-addition salt thereof.

The daily dosage regimen for an adult patient is an oral dose of between 15 mg and 1500 mg and preferably between 20 mg and 250 mg or an intravenous, subcutaneous, or intramuscular dose of between 1.5 mg and 150 mg, and preferably between 5 mg and 20 mg of compound of formula (1) or pharmaceutically acceptable salt thereof calculated as the free base, the composition being administered 1 to 6 times per day.

The pharmaceutical compositions of the invention will normally be administered to man for the treatment of peptic ulcers and other conditions caused or exacerbated by gastric acidity in the same general manner as that employed for known histamine $H_2$-antagonists, due allowance being made in terms of dose levels for the potency of the compounds of the present invention relative to known histamine $H_2$-antagonists.

The following Examples illustrate the invention.

EXAMPLES

EXAMPLE 1

(a) Benzoyl peroxide (8.11 g, 25% water) was dissolved in carbon tetrachloride (900 ml) and the solution dried over magnesium sulphate, filtered and 2-bromo-4-methylpyridine (79.28 g) and N-bromosuccinimide (90.2 g) were added and the mixture was stirred under reflux for 17 hours. The reaction mixture was cooled, filtered and concentrated to ca. 300 ml, washed with 275 ml of each of 4% sodium hydroxide solution, water and then 2% hydrobromic acid. Each aqueous extract in turn was re-extracted with a small volume of carbon tetrachloride. The combined organic layers were diluted with ether (220 ml) and the solution dried over magnesium sulphate and filtered.

The solution was cooled to 4° C. and stirred while a solution of dimethylamine (47.6 g, 70 ml) in ether (130 ml) was added dropwise over 1 hour, the temperature not being allowed to exceed 5° C. After stirring for 2 hours at ca. 0° C. and standing overnight the mixture was extracted with water (2×200 ml) and the aqueous extracts were re-extracted with ether (150 ml). The combined organic extracts were concentrated to remove the solvents and the residue was extracted with ether (200 ml). The combined ether extracts were extracted with dilute acetic acid, the acid extract was basified with sodium carbonate, extracted with ether (3×200 ml) and the combined ether extracts were dried over magnesium sulphate and concentrated to give 2-bromo-4-dimethylaminomethylpyridine as a light amber oil (33.96 g).

(b) Sodium hydride (4.5 g) was suspended in tetrahydrofuran (175 ml) and 3-amino-1-propanol (13.26 g, 13.5 ml) was slowly added. The mixture was stirred and heated under reflux for 30 minutes and then allowed to cool. A solution of 2-bromo-4-dimethylaminomethylpyridine (20.93 g) in tetrahydrofuran (30 ml) was slowly added and the mixture was stirred under reflux for 72 hours. The solvent was removed in vacuo, the residue was dissolved in water (200 ml), and the solution was extracted with dichloromethane (3×150 ml). The combined organic extracts were washed with water (2×10 ml), dried over magnesium sulphate and concentrated to give 3-(4-dimethylaminomethylpyridyl-2-oxy)-propylamine as a light brown oil (19.5 g).

(c) 3-(4-Dimethylaminomethylpyridyl-2-oxy)-propylamine (2.09 g) and dimethylcyanodithioimidocarbonate (2.0 g) were stirred for 20 hours in ethanol (10 ml) at room temperature. Evaporation of the reaction mixture gave a yellow oil which was washed with petroleum ether (b.p. 60°–80° C.). The last traces of petroleum ether were removed in vacuo to give N-cyano-S-methyl-N$^1$-(3-[4-dimethylaminomethylpyridyl-2-oxy]propyl)isothiourea in quantitative yield. The material was used without further purification for the next step.

(d) N-Cyano-S-methyl-N$^1$-(3-[4-dimethylaminomethylpyridyl-2-oxy]propyl)isothiourea (3.0 g) and methyl hydrazine (3.0 ml) were stirred in dimethylformamide (10 ml) at room temperature for 20 hours. The reaction mixture was concentrated to give 1-methyl-N$^5$-3-(4-dimethylaminomethyl-pyridyl-2-oxy)propyl-1H-1,2,4-triazole-3,5-diamine as an oil which was washed with petroleum ether and isolated as the dioxalate. After recrystallisation from methanol 1-methyl-N$^5$-3-(4-dimethylaminomethyl-pyridyl-2-oxy)propyl-1H-1,2,4-triazole-3,5-diamine dioxalate was obtained (1.9 g) m.p. 133°–134° C.

EXAMPLE 2

(a) 3-(4-[1-Piperidinomethyl]-pyridyl-2-oxy)propylamine (4.76 g) and dimethylcyanodithioimidocarbonate (3.01 g) were stirred for 20 hours in ethanol (50 ml) at room temperature. Evaporation of the reaction mixture gave a yellow oil which was washed with petroleum ether (60°–80° C.), the last traces of petroleum ether were removed in vacuo to give N-cyano-S-methyl-N$^1$-(3-[4-(1-piperidinomethyl)-pyridyl-2-oxy]propyl)isothiourea in quantitative yield. The material was used without further purification for the next step.

(b) N-cyano-S-methyl-N$^1$-(3-[4-(1-piperidinomethyl)-pyridyl-2-oxy]propyl)isothiourea (1.35 g) and hydrazine hydrate (1.35 ml) were stirred in dimethylformamide (5 ml) at room temperature for 16 hours. The reaction mixture was concentrated to give a yellow oil which was triturated first with n-hexane then with ether to give a cream coloured solid which was recrystallised from toluene to give N$^5$-3-(4-[1-piperidinomethyl]-pyridyl-2-oxy)propyl-1H-1,2,4-triazole-3,5-diamine (0.7 g) m.p. 139°–140° C. This was converted to the dioxalate with oxalic acid in ethanol m.p. 158°–159° C.

EXAMPLE 3

N-cyano-S-methyl-N$^1$-(3-[4-(1-piperidinomethyl)-pyridyl-2-oxy]propyl)isothiourea (1.5 g) and methyl hydrazine (1.5 ml) were stirred in dimethylformamide (15 ml) at room temperature for 48 hours. The reaction mixture was concentrated to give 1-methyl-N$^5$-3-(4-[1-piperidinomethyl]-pyridyl-2-oxy)propyl-1H-1,2,4-triazole-3,5-diamine as a yellow oil which was washed with petroleum ether and isolated as the dioxalate. After recrystallisation from methanol-isopropanol 1-methyl-N$^5$-3-(4-[1-piperidinomethyl]-pyridyl-2-oxy)-propyl-1H-1,2,4-triazole-3,5-diamine dioxalate was obtained as cream coloured crystals (0.9 g) m.p. 99°–100° C.

EXAMPLE 4

N-Cyano-1-methyl-2-(phenylmethylene)hydrazinecarboximidothioic acid methyl ester (26 g) was added to a solution of 3-(4-[1-piperidinomethyl]-pyridyl-2-oxy)propylamine (28 g) in ethanol (280 ml) and the mixture was stirred at room temperature for 48 hours. The mixture was then diluted with aqueous hydrochloric acid (2M; 225 ml) and the diluted mixture was allowed to stand for 3.5 hours.

The aqueous mixture was extracted with ether, the ether extracts were washed with water and the ether extracts were discarded. The aqueous layer and water washings were combined. The combined aqueous solution was made alkaline to pH8 with sodium hydroxide (2M). The alkaline solution was extracted with chloroform, the chloroform extracts were dried (Na$_2$SO$_4$) and evaporated to give 1-methyl-N5-3-(4-[1-piperidinomethyl]-pyridyl-2-oxy)propyl-1H-1,2,4-triazole-3,5-diamine as a brown oil. The amine was purified by converting it into the dioxalate, i.e. by dissolving it in ethanol (50 ml) reacting it with oxalic acid (28 g) in ethanol (50 ml) and precipitating the salt by adding isopropanol (50 ml). The precipitate was removed by titration and recrystallised from methanol/isopropanol to yield 1-methyl-N5-3-(4-[1-piperidinomethyl]-pyridyl-2-oxy)-propyl-1H-1,2,4-triazole-3,5-diamine-dioxalate (37.0 g).

The dioxalate salt (37.0 g) was dissolved in water (200 ml) and made alkaline to pH12 with sodium hydroxide solution (10 ml) and the alkaline solution extracted with chloroform. The chloroform extract was dried (Na$_2$SO$_4$). Crystallisation of the oil from acetonitrile/ether gave 1-methyl-N5-3-(4-[1-piperidinomethyl]-pyridyl-2-oxy)propyl-1H-1,2,4-triazole-3,5-diamine (20.5 g) m.p. 113°–114° C.

EXAMPLE 5

Pharmaceutical Compositions

A pharmaceutical composition for oral administration is prepared containing

| | % by weight |
|---|---|
| 1-Methyl-N$^5$—3-(4-[1-piperidinomethyl]-2-oxy)propyl-1H—1,2,4-triazole-3,5-diamine | 55 |
| Dibasic calcium phosphate dihydrate | 20 |
| Approved colouring agent | 0.5 |
| Polyvinylpyrrolidone | 4.0 |
| Microcrystalline Cellulose | 8.0 |
| Maize Starch | 8.0 |
| Sodium glycollate | 4.0 |
| Magnesium Stearate | 0.5 | by mixing together the ingredients A (substituting lactose or microcrystalline cellose for dibasic calcium phosphate dihydrate if desired), adding a concentrated solution of polyvinylpyrrolidone and granulating, drying and screening the dried granules; adding the ingredients B to the dried granules and compressing the mixture into tablets containing 100 mg, 150 mg or 200 mg of the free base.

A pharmaceutical composition for injectable administration is prepared by converting 1-methyl-N$^5$-3-(4-[1-piperidinomethyl]-2-oxy)propyl-1H-1,2,4-triazole-3,5-diamine into the dioxalate salt form and dissolving this in sterile pyrogen-free water to give a 1 to 5% w/w solution. The solution is clarified by filtration and filled into vials which are sealed and sterilised. A suitable vial contains 2 ml of the solution.

We claim:

1. A compound of formula (1):

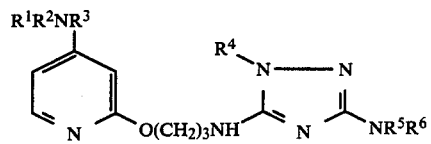

or a pharmaceutically acceptable salt thereof, where
   $R^1$ and $R^2$ are the same or different and are $C_{1-6}$ alkyl or with the nitrogen atom to which they are attached form a pyrrolidino or piperidino group;
   $R^3$ is methylene;
   $R^4$ is hydrogen, $C_{1-6}$ alkyl, hydroxy-$C_{2-4}$ alkyl; optionally substituted phenyl or phenyl ($C_{1-6}$ alkyl) (the substituents being one or more $C_{1-6}$ alkyl, or $C_{1-6}$ alkoxy groups or halogen atoms);
   $R^5$ and $R^6$ are hydrogen.

2. A compound according to claim 1 where $R^1$ and $R^2$ are the same and are $C_{1-6}$ alkyl.

3. A compound according to claim 2, where $R^1$ and $R^2$ are both methyl.

4. A compound according to claim 1, where $R^1R^2NR^3$ is dimethylaminomethyl.

5. A compound according to claim 1 where $R^1R^2N$ represents piperidinyl.

6. A compound according to claim 5, where $R^1R^2NR^3$ is piperidinylmethyl.

7. A compound according to claim 1, where $R^4$ is methyl.

8. A compound according to claim 1 selected from 1-methyl-N$^5$-3-(4-dimethylaminomethyl-pyridyl-2-oxy)-propyl-1H-1,2,4-triazole-3,5-diamine and a pharmaceutically acceptable salt thereof.

9. A compound according to claim 1 selected from N$^5$-3-(4-[1-piperidinomethyl]-pyridyl-2-oxy)propyl-1H-1,2,4-triazole-3,5-diamine and a pharmaceutically acceptable salt thereof.

10. A compound according to claim 1 selected from 1-methyl-N$^5$-3-(4-[1-piperidinomethyl]-pyridyl-2-oxy)-propyl-1H-1,2,4-triazole-3,5-diamine and a pharmaceutically acceptable salt thereof.

11. A pharmaceutical composition having histamine H$_2$-antagonist activity comprising an amount of a compound according to claim 1 sufficient to block histamine H$_2$ receptors and a pharmaceutically acceptable carrier.

12. A method of blocking histamine H$_2$ receptors which comprises administering to an animal an effective amount to block said receptors of a compound of claim 1.

* * * * *